United States Patent [19]

Yoshino et al.

[11] Patent Number: 4,659,726
[45] Date of Patent: Apr. 21, 1987

[54] NOVEL 4,5-BIS(4-METHOXYPHENYL)-2-(PYRROL-2-YL)THIAZOLES AND PHARMACEUTICAL COMPOSITION CONTAINING THE SAME

[75] Inventors: Koichiro Yoshino, Suita; Norihiko Seko, Osaka; Koichi Yokota, Sakai; Keizo Ito, Osaka; Goro Tsukamoto, Toyonaka, all of Japan

[73] Assignee: Kanebo, Ltd., Tokyo, Japan

[21] Appl. No.: 722,322

[22] Filed: Apr. 12, 1985

[30] Foreign Application Priority Data

Apr. 19, 1984 [JP] Japan .................................. 59-79924
Jul. 25, 1984 [JP] Japan ................................. 59-156184
Feb. 28, 1985 [JP] Japan .................................. 60-40802

[51] Int. Cl.[4] ................. A61K 31/425; C07D 277/24; C07D 277/28
[52] U.S. Cl. ..................................... 514/365; 548/205
[58] Field of Search ........................ 548/205; 514/365

[56] References Cited

U.S. PATENT DOCUMENTS 4,168,315 9/1979 Rynbrandt et al. ................. 514/365
4,322,428 3/1982 Matsumoto et al. ................ 574/365
4,466,976 8/1984 Klose et al. ......................... 548/205

OTHER PUBLICATIONS

Rynbrandt et al., *J. Med. Chem.*, vol. 24, pp. 1507–1510, 1981.

Primary Examiner—Donald G. Daus
Assistant Examiner—Stephen Kapner
Attorney, Agent, or Firm—Wegner & Bretschneider

[57] ABSTRACT

Novel 4,5-bis(4-methoxyphenyl)-2-(pyrrol-2-yl)thiazoles of the formula:

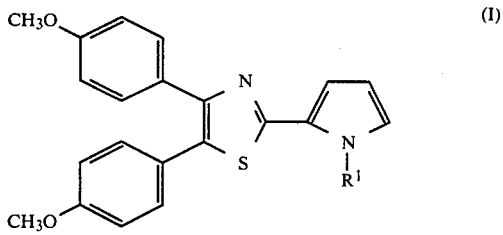

wherein $R^1$ is $C_{1-4}$ alkyl, $C_{2-4}$ alkenyl, $C_{2-4}$ alkynyl, 2,2,2-trifluoroethyl, a group of the formula: $-CH_2COOR^2$ $R^2$ is $C_{1-8}$ alkyl, $C_{2-4}$ alkenyl, $C_{2-4}$ alkynyl, or phenyl-$C_{1-2}$ alkyl), or a group of the formula: $-(CH_2)_n-A-R^3$ (A is oxygen or sulfur, $R^3$ is $C_{1-4}$ alkyl or $C_{2-4}$ alkenyl, and n is 1, 2 or 3), a process for the preparation of the compounds, and a pharmaceutical composition useful as a platelet aggregation inhibitor which comprises as an active ingredient the above 4,5-bis(4-methoxyphenyl)-2-(pyrrol-2-yl)thiazole compound in admixture with a conventional pharmaceutically acceptable carrier or diluent.

7 Claims, No Drawings

NOVEL 4,5-BIS (4-METHOXYPHENYL)-2-(PYRROL-2-YL) THIAZOLES AND PHARMACEUTICAL COMPOSITION CONTAINING THE SAME

The present invention relates to novel 4,5-bis(4-methoxyphenyl)-2-(pyrrol-2-yl)thiazoles, process for the preparation thereof, and a pharmaceutical composition containing the compounds as an active ingredient. More particularly, it relates to novel compounds of the formula:

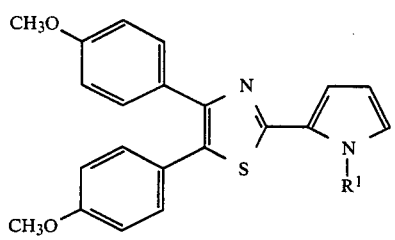

(I)

wherein $R^1$ is an alkyl having 1 to 4 carbon atoms (hereinafter, referred to like "$C_{1-4}$ alkyl"), $C_{2-4}$ alkenyl, $C_{2-4}$ alkynyl, 2,2,2-trifluoroethyl, a group of the formula: —$CH_2COOR^2$ ($R^2$ is $C_{1-8}$ alkyl, $C_{2-4}$ alkenyl, $C_{2-4}$ alkynyl, or phenyl-$C_{1-2}$ alkyl), or a group of the formula: —$(CH_2)_n$—A—$R^3$ (A is oxygen or sulfur, $R^3$ is $C_{1-4}$ alkyl or $C_{2-4}$ alkenyl, and n is 1, 2 or 3), a process for the preparation of the compounds, and a pharmaceutical composition useful as a platelet aggregation inhibitor which comprises as an active ingredient the above 4,5-bis(4-methoxyphenyl)-2-(pyrrol-2-yl)thiazole compound.

PRIOR ART

There have hitherto been clinically used various compounds such as ticlopidine hydrochloride, aspirin, etc. as a platelet aggregation inhibitor.

U.S. Pat. No. 4,168,315 and J. Med. Chem., 24, 1507 (1981) disclose 4,5-diphenyl-2-substituted (or unsubstituted) alkylthiazoles having a platelet aggregation inhibiting activity, among which 4,5-bis(4-methoxyphenyl)-2-trifluoromethylthiazole (Compound A) of the following formula is the representative compound:

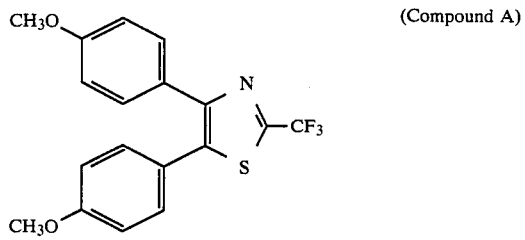

(Compound A)

It is also disclosed in U.S. Pat. No. 4,322,428 that 4,5-bis(4-methoxyphenyl)thiazoles are useful as an anti-inflamatory agent or a platelet aggregation inhibitor. This literature does not disclose specific pharmacological data of the platelet aggregation inhibition, but discloses as a representative compound 4,5-bis(4-methoxyphenyl)-2-(4-fluorophenyl)thiazole (Compound B) of the formula:

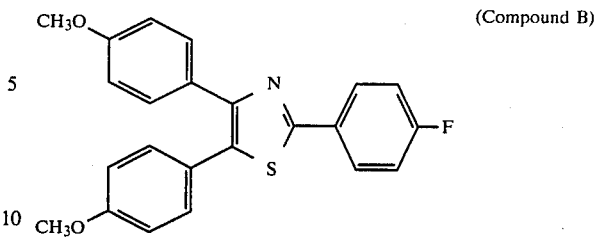

(Compound B)

Besides, European Pat. No. 77,024 discloses 4,5-bis(4-methoxyphenyl)-2-pyrrolylimidazole derivatives having an anti-inflammatory activity, particularly 4,5-bis(4-methoxyphenyl)-2-(1-methylpyrrol-2-yl)imidazole (Compound C) of the formula:

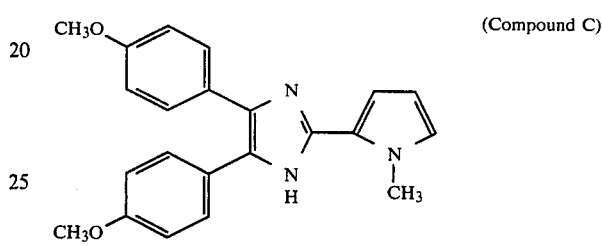

(Compound C)

OBJECT OF INVENTION

The compounds (I) of the present invention show potent inhibitory activity against platelet aggregation with low toxicity, and hence, are useful for the prophylaxis and treatment of various thromboses which are induced by platelet aggregation. Thus, an object of the present invention is to provide novel 4,5-bis(4-methoxyphenyl)-2-(pyrrol-2-yl)thiazoles of the formula (I) which are useful as a platelet aggregation inhibitor. Another object of the invention is to provide a process for the preparation of said compounds. A further object of the invention is to provide a pharmaceutical composition for the prophylaxis and treatment of various thromboses which comprising as an active ingredient the said compound in admixture with a conventional pharmaceutically acceptable carrier or diluent. These and other objects and advantages of the present invention will be apparent to persons skilled in the art from the following description.

DETAILED DESCRIPTION OF INVENTION

The 4,5-bis(4-methoxyphenyl)-2-(pyrrol-2-yl)thiazoles of the present invention have the formula (I) as described hereinbefore.

In the formula (I), the groups for the symbol $R^1$ includes the following groups: $C_{1-4}$ alkyl, i.e. straight or branched chain alkyl group having 1 to 4 carbon atoms, such as methyl, ethyl, n-propyl, isopropyl and isobutyl; $C_{2-4}$ alkenyl such as allyl; $C_{2-4}$ alkynyl such as propargyl; 2,2,2-trifluoroethyl; a group of the formula: —$CH_2COOR^2$ ($R^2$ is $C_{1-8}$ alkyl, i.e. straight or branched chain alkyl groups, such as methyl, ethyl, n-propyl, isopropyl, n-butyl, isobutyl, sec-butyl, n-pentyl, isopentyl, neopentyl, 2-pentyl, 3-pentyl, 2-methyl-1-butyl, 3-methyl-2-butyl, n-hexyl, and n-octyl; $C_{2-4}$ alkenyl such as allyl; $C_{2-4}$ alkynyl such as propargyl; or phenyl-$C_{1-2}$ alkyl such as benzyl and phenethyl), or a group of the formula: —$(CH_2)_n$—A—$R^3$ (A is oxygen or sulfur, $R^3$ is $C_{1-4}$ alkyl such as methyl, ethyl and n-propyl, or $C_{2-4}$ alkenyl such as vinyl, and n is 1, 2 or 3).

The compounds (I) can be prepared, for example, by a process as shown in the following reaction scheme-I:

Reaction Scheme-I:

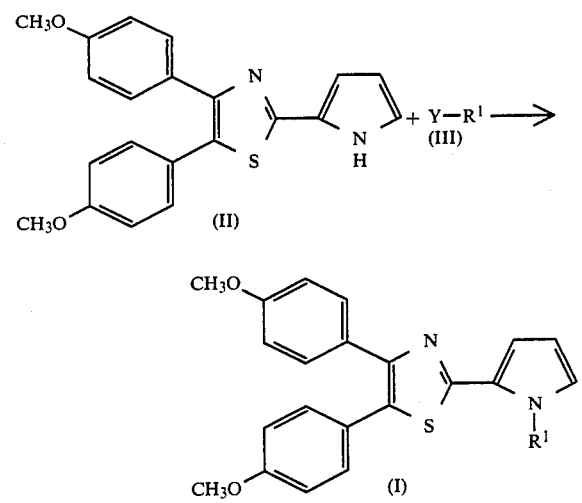

wherein $R^1$ is as defined above, and Y is a halogen such as chlorine, bromine or iodine, or p-toluenesulfonyloxy group.

The process of the above reaction scheme-I can be carried out by reacting a compound (II) and an equimolar or excess amount of a compound (III) in the presence of a base or a phase transfer catalyst. In case of using a base such as metallic potassium, metallic sodium, potassium tertbutoxide, etc., the reaction is carried out in a solvent of tetrahydrofuran or dimethoxyethane at a temperature of from room temperature to a boiling point of the solvent for 1 to 24 hours. In case of using a phase transfer catalyst such as a quaternary ammonium salt (e.g. tetra-n-butylammonium bromide, methyltrioctylammonium chloride, etc.), the reaction is carried out in two phases of benzene or dichloromethane and 50% aqueous sodium hydroxide or 60% aqueous potassium hydroxide at a temperature of from 0° C. to a boiling point of the solvent for one minute to 24 hours.

The starting compound (II) can be prepared in the following reaction scheme-II:

Reaction Scheme-II:

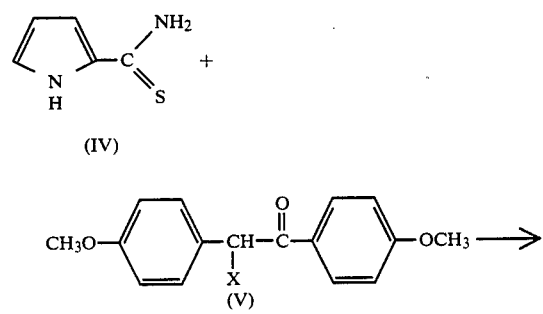

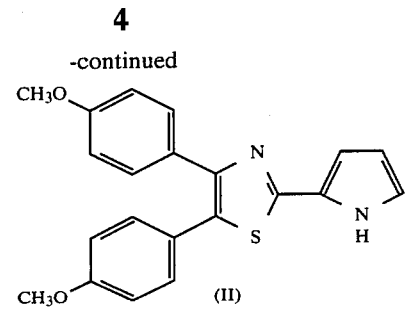

wherein X is a halogen such as bromine or chlorine.

The abvove process can be carried out by reacting a compound (IV) and a equimolar amount of a compound (V) in a solvent such as acetonitrile, dimethylformamide (DMF), dimethyl sulfoxide (DMSO), or an alcohol (e.g. ethanol) at a temperature of from 50° C. to a boiling point of the solvent for 10 minutes to 4 hours.

The compounds of the formula (I) wherein $R^1$ is $C_{1-4}$ alkyl, $C_{2-4}$ alkenyl, $C_{2-4}$ alkynyl, or 2,2,2-trifluoroethyl can also be prepared in a similar manner as shown in the reaction scheme-II, that is by the following reaction scheme-III:

Reaction Scheme-III:

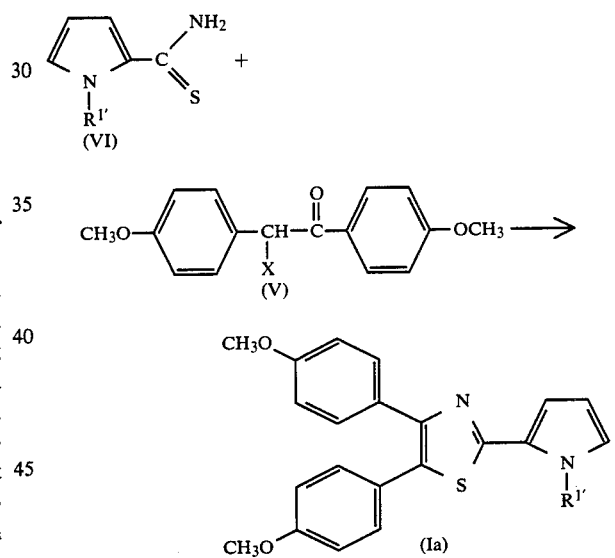

wherein $R^{1'}$ is $C_{1-4}$ alkyl, $C_{2-4}$ alkenyl, $C_{2-4}$ alkynyl, or 2,2,2-trifluoroethyl, and X is as defined above.

The above process can be carried out by reacting a compound (VI) and an equimolar amount of a compound (V) in the same manner as described as to the reaction scheme-II.

The starting compound (VI) in the reaction scheme-III can be prepared by a process as shown in the following reaction scheme-IV:

Reaction Scheme-IV:

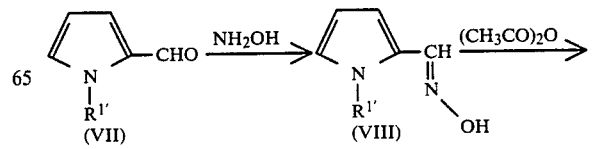

-continued

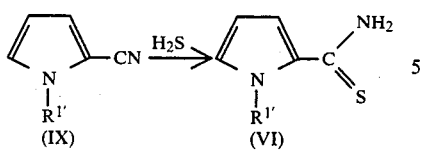

wherein R[1'] is as defined above.

The process can be carried out by converting a compound (VII) into an oxime (VIII) by a conventional oxime forming reaction, heating the oxime (VIII) in acetic anhydride to obtain a compound (IX), and treating the compound (IX) with hydrogen sulfide, that is, by blowing hydrogen sulfide gas into a reaction system containing the compound (IX) in a solvent such as DMF, DMSO or pyridine in the presence of 0.5 to 5 equimolar amount of a base such as a tertiary amine (e.g. triethylamine) at a temperature of from 0° to 40° C. for 3 to 24 hours.

The compounds of the formula (I) wherein $R^1$ is $-CH_2COOR^2$ can also be prepared by a process as shown in the following reaction scheme-V:

Reaction Scheme-V:

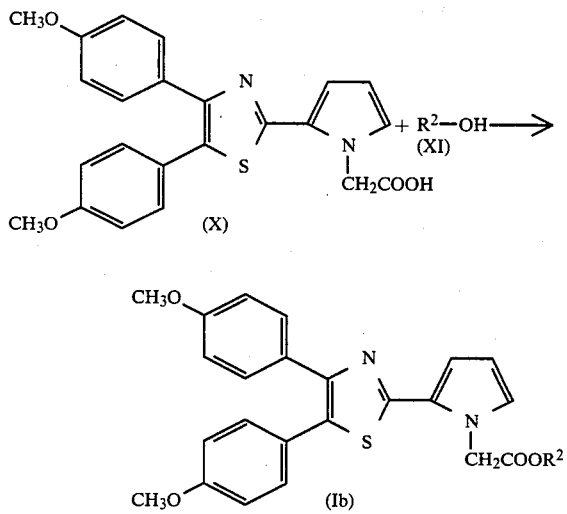

wherein $R^2$ is as defined above.

The process of the reaction scheme-V can be carried out by reacting a compound (X) with a largely excess amount of a compound (XI) at a reflux temperature in the presence of an acid catalyst or by reacting 1 mole of a compound (X) with 1 to 10 moles of a compound (XI) in a solvent such as benzene or toluene at a reflux temperature in the presence of an acid catalyst while distilling off water by azeotropy.

The starting compound (X) can easily be prepared by hydrolysis of a compound of the formula:

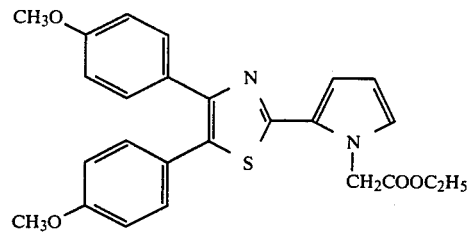

which is prepared by the process as shown in the reaction scheme-I. The hydrolysis can be carried out by a conventional process using an alkali.

The compounds (I) of the present invention have potent platelet aggregation inhibitory activity with low toxicity and hence are useful for the prophylaxis and treatment of various diseases caused by platelet aggregation such as thombosis, ischemic heart disease, and transient ischemic attack.

When the compounds (I) are used for the prophylaxis and treatment of diseases caused by platelet aggregation, they are usually administered to the patients by oral route.

For oral administration, the compounds (I) are used in the form of a conventional preparation, for example, solid preparations, such as tablets, granules, powders, fine granules, hard capsules, and liquid preparations, such as syrups, soft capsules. These preparations can be prepared by a conventional method. For example, the solid preparations can be prepared by admixing the active compounds (I) with conventional carriers, such as lactose, starches, crystalline cellulose, talc, etc. The hard capsules are prepared by packing granules or fine granules containing the active compounds (I) in hard capsules. Syrups can be prepared by dissolving or suspending the compounds (I) in an aqueous solution of lactose, carboxymethyl cellulose, etc. Soft capsules can be prepared by packing a mixture of the compounds (I) with vegetable oils, oily emulsion, glycol, etc. in soft capsules.

Dose of the compounds (I) may vary according to the kinds and severity of the diseases, weight and age of the patients, and the like, but is usually in the range of 1 to 100 mg per day in adult, which may be used at once or divided into two or three times.

The following are experimental results of platelet aggregation inhibitory activity and acute toxicity.

Experiment 1

Platelet aggregation inhibitory activity:
Test compounds:
 1. The compounds of the present invention as prepared in Examples disclosed hereinafter.
 2. Compounds A, B and C (reference compounds) which are disclosed in literatures as mentioned hereinbefore.
 3. Ticlopidine hydrochloride (reference compound) which is known as a platelet aggregation inhibitor.
 4. Aspirin (reference compound) which is known as a platelet aggregation inhibitor.
Method:
Hartley strain male guinea pigs (weighing 300–350 g, one group: three animals) were fasted overnight, and to the animals were orally administered a solution or suspension of the test compounds in corn oil-10% arabic gum. After 3 hours, blood was collected from the abdominal aorta into a syringe containing 3.8% aqueous sodium citrate solution to obtain a citrated blood (1/10 part of citrate solution:9/10 parts of blood). The citrated blood thus obtained was centrifuged at 1,700 rpm for 10 minutes, and a platelet-rich plasma (PRP) was obtained from the supernatant. After isolating PRP, the remaining blood was further centrifuged at 3,000 rpm for 10 minutes, and a platelet-poor plasma (PPP) was obtained from the supernatant.

The PRP (450 μl) thus obtained was incubated at 37° C. for 3 minutes, and thereto was added 1.0 mM sodium arachidonate (50 μl) as an aggregating agent, and then the platelet aggregation thereof was measured with Platelet Aggregation Profiler ® (Model PAP-3, manufactured by Bio Data Corp.) while using the PPP obtained above as a blank. As a control, as to animals to which no test compound was administered, the platelet aggregation rate was measured likewise.

The platelet aggregation inhibitory rate was calculated by the following equation.

Platelet aggregation inhibitory rate (%) =

$$\left( \frac{\text{Extent of platelet aggregation in the test compound-administered group}}{\text{Extent of latelet aggregation in the control group}} \right) \times 100$$

Besides, the dose of the test compound which can give 50% inhibitory rate (ED$_{50}$) was determined by regression analysis.

Moreover, the above method was repeated except that 100 μg/ml collagen suspension (50 μl) was used as an aggregating agent instead of sodium arachidonate.
Results:
The experimental results are shown in Table 1.

Experiment 2

Acute toxicity:
Test compounds:
The same as in the above Experiment 1.
Method:
ddy male mice (weighing 18–23 g, one group: 5 animals) were fasted overnight, and thereto was orally administered a suspension of the test compounds in 1% arabic gum solution. Number of died animal was counted at 10 days after the administration, and the 50% lethal dose (LD$_{50}$) was calculated by Weil method.
Results:
The results are shown in Table 1.

TABLE 1

| Test compound | Platelet aggregation inhibitory activity | | Acute toxicity LD$_{50}$ (mg/kg) |
|---|---|---|---|
| | Arachidonate ED$_{50}$ (mg/kg) | Collagen ED$_{50}$ (mg/kg) | |
| Ex. 1 | 0.47 | 0.91 | >3000 |
| Ex. 2 | 0.29 | 0.63 | >3000 |
| Ex. 3 | 0.32 | 0.52 | >3000 |
| Ex. 4 | 0.41 | 0.78 | >3000 |
| Ex. 5 | 0.40 | 0.55 | >3000 |
| Ex. 6 | 0.22 | 0.92 | >3000 |
| Ex. 7 | 0.47 | 0.51 | >3000 |
| Ex. 13 | 0.26 | 0.89 | >3000 |
| Ex. 14 | 0.088 | 0.19 | >3000 |
| Ex. 15 | 0.072 | 0.11 | >3000 |
| Ex. 16 | 0.061 | 0.11 | >3000 |
| Ex. 17 | 0.15 | 0.19 | >3000 |
| Ex. 18 | 0.072 | 0.12 | >3000 |
| Ex. 19 | 0.12 | 0.11 | >3000 |
| Ex. 20 | 0.28 | 0.49 | >3000 |
| Ex. 21 | 0.12 | 0.22 | >3000 |
| Ex. 22 | 0.11 | 0.40 | >3000 |
| Ex. 23 | 0.073 | 0.14 | >3000 |
| Ex. 24 | 0.12 | 0.22 | >3000 |
| Ex. 25 | 0.12 | 0.34 | >3000 |
| Ex. 26 | 0.26 | 0.34 | >3000 |
| Ex. 27 | 0.21 | 0.22 | >3000 |
| Ex. 28 | 0.39 | 0.44 | >3000 |
| Ex. 29 | 0.047 | 0.11 | >3000 |
| Ex. 30 | 0.039 | 0.068 | >3000 |
| Ex. 31 | 0.11 | 0.16 | >3000 |
| Ex. 36 | 0.45 | 0.98 | >3000 |
| Ex. 37 | 0.49 | 0.61 | >3000 |
| Ex. 38 | 0.09 | 0.29 | >3000 |
| Ex. 39 | 0.33 | 0.49 | >3000 |
| Ex. 40 | 0.41 | 0.51 | >3000 |
| Ex. 41 | 0.30 | 0.35 | >3000 |
| Compd. A | 0.54 | 1.29 | >3000 |
| Compd. B | 1.24 | 1.20 | >3000 |
| Compd. C | 1.21 | 2.51 | >3000 |
| Ticlopidine.HCl | >300 | 300 | 804 |
| Aspirin | 38.2 | 58.9 | 1061 |

As is clear from the above experimental results, the compounds (I) of the present invention show superior platelet aggregation inhibitory activity than the known platelet aggregation inhibitors such as ticlopidine hydrochloride and aspirin and further than the known Compounds A, B and C which have a similar chemical structure to that of the compounds (I) of the present invention. Moreover, the compounds (I) have less toxicity. Accordingly, the compounds (I) are very useful for the prophylaxis and treatment of various diseases caused by platelet aggregation.

The compounds (I) of the present invention and processes of the preparation thereof are illustrated by the following Reference Examples and Examples.

Reference Example 1

1-Ethylpyrrole-2-carbothioamide (compound of the formula (VI), wherein R$^{1'}$=ethyl):
(1) 1-Ethylpyrrole-2-carbonitrile:
1-Ethylpyrrole-2-carbaldehyde (cf. J. Chem. Soc. (C), 2563, 1970) (7.4 g, 60 mmole), hydroxylamine hydrochloride (4.8 g, 69 mmole) sodium acetate trihydrate (9.4 g, 69 mmole) and water (30 ml) are mixed, and the mixture is stirred at room temperature for 20 minutes and then allowed to stand in a cooled place overnight. The precipitated oxime compound is taken by filtration and dried. The oxime compound is refluxed in acetic anhydride (25 ml) for 20 minutes and then allowed to cool until room temperature. The reaction mixture is added to ice water, and the mixture is stirred for 2 hours and neutralized with sodium carbonate and extracted with ether twice. The ether layer is dried over anhydrous magnesium sulfate, and the solvent is distilled off under reduced pressure. The resulting residue is distilled under reduced pressure to give 1-ethylpyrrole-2-carbonitrile (5.25 g, yield: 73%).

B.p. 71°–74° C./6 mmHg
NMR (CDCl$_3$, δppm): 1.4 (3H, t), 4.1 (2H, q), 6.1 (1H, dd), 6.6–7.0 (2H).
(2) 1-Ethylpyrrole-2-carbothioamide:

The 1-ethylpyrrole-2-carbonitrile obtained above (3.0 g, 25 mmole) is dissolved in a solution of triethylamine (12.5 g, 125 mmole) in pyridine (13 ml), and therein hydrogen sulfide is blown at 20° C. for 6 hours. To the reaction mixture is added water (300 ml). The precipitated crystals are separated by filtration, dried, and then recrystallized from ligroin to give 1-ethylpyrrole-2-carbothioamide (2.5 g, yield: 65%).

M.p. 71.5°–74.5° C.

Reference Example 2

1-Isopropylpyrrole-2-carbothioamide (compound of the formula (VI), wherein $R^{1'}$=isopropyl):
(1) 1-Isopropylpyrrole-2-carbonitrile:

1-Isopropylpyrrole-2-carbaldehyde (cf. J. Chem. Soc. (C), 2563, 1970) (8.2 g, 60 mmole), hydroxylamine hydrochloride (4.8 g, 69 mmole), sodium acetate trihydrate (9.4 g, 69 mmole) and water (30 ml) are mixed, and the mixture is stirred at 70° C. for 1.5 hour and then allowed to cool until room temperature. The reaction mixture is extracted with ether twice. The ether layer is dried over anhydrous magnesium sulfate, and the solvent is distilled off under reduced pressure to give an oily oxime compound. The oxime compound is refluxed in acetic anhydride (25 ml) for 20 minutes and then allowed to cool until room temperature. The reaction mixture is poured into ice water, and the mixture is stirred for 2 hours and then neutralized with sodium carbonate. The mixture is extracted with ether twice. The ether layer is dried over anhydrous magnesium sulfate, and the solvent is distilled off under reduced pressure. The resulting residue is distilled under reduced pressure to give 1-isopropylpyrrole-2-carbonitrile (5.7 g, yield: 71%).

B.p. 78°–81° C./5.5 mmHg

NMR (CDCl$_3$, δppm): 1.5 (6H, d), 4.5 (1H), 6.1 (1H, dd), 6.7 (1H, dd), 6.9 (1H, dd).

(2) 1-Isopropylpyrrole-2-carbothioamide:

The 1-isopropylpyrrole-2-carbonitrile obtained above (3.35 g, 25 mmole) is treated in the same manner as described in Reference Example 1 (2) to give 1-isopropylpyrrole-2-carbothioamide (3.85 g, yield: 92%).

M.p. 97.5°–100.5° C.

Reference Example 3

1-n-Propylpyrrole-2-carbothioamide (compound of the formula (VI), wherein $R^{1'}$=n-propyl):
(1) 1-n-Propylpyrrole-2-carbonitrile:

In the same manner as described in Reference Example 2 (1) except that 1-n-propylpyrrole-2-carbaldehyde (prepared in the same manner as described in Can. J. Chem., 55, 4112, 1977, b.p. 72°–75°C./5 mmHg) (8.2 g, 60 mmole) is used instead of 1-isopropylpyrrole-2-carbaldehyde and further the product is isolated by silica gel column chromatography (solvent: dichloromethane) instead of distillation under reduced pressure, there is obtained 1-n-propylpyrrole-2-carbonitrile (3.6 g, yield: 45%).

NMR (CDCl$_3$, δppm): 0.9 (3H, t), 1.5-2.1 (2H), 3.9 (2H, t), 6.1 (1H, dd), 66.-6.9 (2H).

(2) 1-n-Propylpyrrole-2-carbothioamide:

The 1-n-propylpyrrole-2-carbonitrile obtained above (3.35 g, 25 mmole) is treated in the same manner as described in Reference Example 1 (2) to give 1-n-propylpyrrole-2-carbothioamide (3.35 g, yield: 80%).

M.p. 88°–91° C.

Reference Example 4

1-Isobutylpyrrole-2-carbothioamide (compound of the formula (VI), wherein $R^{1'}$=isobutyl):
(1) 1-Isobutylpyrrole-2-carbonitrile:

In the same manner as described in Reference Example 2 (1) except that 1-isobutylpyrrole-2-carbaldehyde (cf. J. Agr. Food. Chem., 22, 279, 1974) (9.1 g, 60 mmole) is used instead of 1-isopropylpyrrole-2-carbaldehyde, there is obtained 1-isobutylpyrrole-2-carbonitrile (6.6 g, yield: 74%).

B.p. 84°–87° C./5 mmHg

NMR (CDCl$_3$, δppm): 0.9 (6H, d), 1.7–2.0 (1H), 3.8 (2H, d), 6.1 (1H, dd), 6.6–6.9 (2H).

(2) 1-Isobutylpyrrole-2-carbothioamide:

The 1-isobutylpyrrole-2-carbonitrile obtained above (3.7 g, 25 mmole) is treated in the same manner as described in Reference Example 1 (2) to give 1-isobutylpyrrole-2-carbothioamide (4.05 g, yield: 89%).

M.p. 125.5°–128.5° C.

Reference Example 5

1-Allylpyrrole-2-carbothioamide (compound of the formula (VI), wherein $R^{1'}$=allyl):
(1) 1-Allylpyrrole-2-carbonitrile:

In the same manner as described in Reference Example 2 (1) except that 1-allylpyrrole-2-carbaldehyde (prepared in the same manner as described in Can. J. Chem., 55, 4112, 1977, b.p. 80°–83° C./7 mmHg) (8.1 g, 60 mmole) is used instead of 1-isopropylpyrrole-2-carbaldehyde and further the product is isolated by silica gel column chromatography (solvent, cyclohexane:dichloromethane=3:1) instead of distillation under reduced pressure, there is obtained 1-allylpyrrole-2-carbonitrile (4.0 g, yield: 50%).

NMR (CDCl$_3$, ppm): 4.5–4.7 (2H), 4.8–5.4 (2H), 5.6–6.0 (1H), 6.2 (1H, dd), 6.6–6.9 (2H).

(2) 1-Allylpyrrole-2-carbothioamide:

The 1-allylpyrrole-2l -carbonitrile obtained above (3.3 g, 25 mmole) is treated in the same manner as described in Reference Example 1 (2) to give 1-allylpyrrole-2-carbothioamide (2.45 g, yield: 59%).

M.p. 80.5°–83.0° C.

Reference Example 6

4,5-Bis(4-methoxyphenyl)-2-(pyrrol-2-yl)-thiazole [compound of the formula (II)]:

Pyrrole-2-carbothioamide (cf. J. Org. Chem., 38, 667, 1973) (1.51 g, 12 mmole) and α-bromo-4,4'-dimethoxydeoxybenzoin (cf. Aust. J. Chem., 8, 385. 1955) (4.02 g, 12 mmole) are dissolved in acetonitrile (120 ml). The mixture is stirred at 60° C. for 50 minutes. After the reaction, the reaction mixture is distilled under reduced pressure to remove the solvent. To the resulting residue are added chloroform and aqueous solution of sodium carbonate, and the mixture is shaken. The chloroform layer is taken, and the aqueous layer is further extracted with chloroform. The chloroform layers are combined, dried over anhydrous magnesium sulfate, and distilled under reduced pressure to remove the solvent. The residue is recrystallized from ligroin to give 4,5-bis(4-methoxyphenyl)-2-(pyrrol-2-yl)-thiazole (3.74 g, yield: 86%).

M.p. 131.5°–134.0° C.

NMR (CDCl$_3$, δppm): 3.7 (6H), 6.1 (1H, dd), 6.5–6.9 (6H), 7.1–7.5 (4H), 9.4–9.8 (1H).

Elementary analysis for $C_{21}H_{18}N_2O_2S$: Calcd. (%): C, 69.59; H, 5.01; N, 7.73; Found (%): C, 70.06; H, 4.90; N, 7.68.

Reference Example 7

2-[4,5-Bis(4-methoxyphenyl)thiazol-2-yl]pyrrole-1-acetic acid [compound of the formula (X)]:

Ethyl 2-[4,5-bis(4-methoxyphenyl)thiazol-2-yl]-pyrrole-1-acetate (prepared in Example 14) (3.59 g, 8 mmole) and potassium hydroxide (0.90 g, 16 mmoles) are added to ethanol (80 ml), and the mixture is refluxed for 5 minutes. After distilling off ethanol, the resulting residue is dissolved in water. To the aqueous solution is added 10% hydrochloric acid, and the precipitated crystals are separated by filtration and dried to give crude crystals (3.20 g). The crude crystals are recrystallized from benzene to give 2-[4,5-bis(4-methoxyphenyl)-thiazol-2-yl]-pyrrole-1-acetic acid (2.69 g, yield: 80%).

M.p. 197.5°–200.5° C.

NMR (DMSO-d$_6$, δppm): 3.75 (3H, s), 3.8 (3H, s), 5.25 (2H, s), 6.15 (1H, dd), 6.75 (1H, dd), 6.8–7.1 (5H), 7.2–7.55 (4H), 12.3–13.1 (1H).

Elementary analysis for $C_{23}H_{20}N_2O_4S$: Calcd. (%): C, 65.70; H, 4.79; N, 6.66; Found (%): C, 65.75; H, 4.74; N, 6.48.

EXAMPLE 1

4,5-Bis(4-methoxyphenyl)-2-(1-ethylpyrrol-2-yl)-thiazole (compound of the formula (I) wherein $R^1$=ethyl):

1-Ethylpyrrole-2-carbothioamide obtained in Reference Example 1 (1.85 g, 12 mmole) and α-bromo-4,4'-dimethoxydeoxybenzoin (cf. Aust. J. Chem., 8, 385, 1955) (4.02 g, 12 mmole) are dissolved in acetonitrile (120 ml), and the mixture is stirred at 60° C. for 50 minutes. After the reaction, the mixture is distilled under reduced pressure to remove the solvent. To the residue are added chloroform and aqueous sodium carbonate, and the mixture is shaken. The chloroform layer is taken, and the aqueous layer is further extracted with chloroform. The chloroform layers are combined, dried over anhydrous magnesium sulfate, and distilled under reduced pressure to remove the solvent. The residue is recrystallized from n-hexane to give 4,5-bis(4-methoxyphenyl)-2-(1-ethylpyrrol-2-yl)thiazole (3.6 g, yield: 77%).

M.p. 76.5°–79.5° C.

NMR (CDCl$_3$, δppm): 1.5 (3H, t), 3.8 (6H), 4.55 (2H, q), 6.15 (1H, dd), 6.65 (1H, dd), 6.75–6.95 (5H), 7.2–7.6 (4H).

Elementary analysis for $C_{23}H_{22}N_2O_2S$: Calcd. (%): C, 70.74; H, 5.68; N, 7.71; Found (%): C, 70.84; H, 5.60; N, 7.11.

EXAMPLE 2

4,5-Bis(4-methoxyphenyl)-2-(1-isopropylpyrrol-2-yl)thiazole (compound of the formula (I) wherein $R^1$=isopropyl):

1-Isopropylpyrrole-2-carbothioamide obtained in Reference Example 2 (2.02 g, 12 mmole) is treated in the same manner as described in Example 1 to give 4,5-bis(4-methoxyphenyl)-2-(1-isopropylpyrrol-2-yl)thiazole (3.30 g, yield: 68%).

M.p. 72.5°–75.5° C.

NMR (CDCl$_3$, δppm): 1.5 (6H, d), 3.8 (6H), 5.7 (1H), 6.2 (1H, dd), 6.65 (1H, dd), 6.75–7.05 (5H), 7.2–7.6 (4H).

Elementary analysis for $C_{24}H_{24}N_2O_2S$: Calcd. (%): C, 71.26; H, 5.98; N, 6.93; Found (%): C, 71.54; H, 6.03; N, 7.02.

EXAMPLE 3

4,5-Bis(4-methoxyphenyl)-2-(1-n-propylpyrrol-2-yl)thiazole (compound of the formula (I) wherein $R^1$=n-propyl):

1-n-Propylpyrrole-2-carbothioamide obtained in Reference Example 3 (2.02 g, 12 mmole) is treated in the same manner as described in Example 1 to give 4,5-bis(4-methoxyphenyl)-2-(1-n-propylpyrrol-2-yl)thiazole (2.42 g, yield: 50%).

M.p. 77°–80° C.

NMR (CDCl$_3$, δppm): 0.95 (3H, t), 1.7–2.1 (2H), 3.8 (6H), 4.4 (2H, t), 6.1 (1H, dd), 6.5–6.95 (6H), 7.1–7.6 (4H).

Elementary analysis for $C_{24}H_{24}N_2O_2S$: Calcd. (%): C, 71.26 H, 5.98; N, 6.93; Found (%): C, 71.19; H, 6.05; N, 6.97.

EXAMPLE 4

4,5-Bis(4-methoxyphenyl)-2-(1-isobutylpyrrol-2-yl)thiazole (compound of the formula (I) wherein $R^1$=isobutyl):

1-Isobutylpyrrole-2-carbothioamide obtained in Reference Example 4 (2.19 g, 12 mmole) is treated in the same manner as described in Example 1 to give 4,5-bis(4-methoxyphenyl)-2-(1-isobutylpyrrol-2-yl)thiazole (2.56 g, yield: 51%).

M.p. 76°14 79° C.

NMR (CDCl$_3$, δppm): 0.95 (6H, d), 2.1–2.55 (1H), 3.8 (6H), 4.3 (2H, d), 6.15 (1H, dd), 6.6–6.95 (6H), 7.2–7.6 (4H).

Elementary analysis for $C_{25}H_{26}N_2O_2S$: Calcd. (%): C, 71.74; H, 6.26; N, 6.69; Found (%): C, 72.00; H, 6.36; N, 6.68.

EXAMPLE 5

4,5-Bis(4-methoxyphenyl)-2-(1-allylpyrrol-2-yl)-thiazole (compound of the formula (I) wherein $R^1$=allyl):

1-Allylpyrrole-2-carbothioamide obtained in Reference Example 5 (1.99 g, 12 mmole) is treated in the same manner as described in Example 1 to give 4,5-bis(4-methoxyphenyl)-2-(1-allylpyrrol-2-yl)thiazole (3.04 g, yield: 63%).

M.p. 57°–60° C.

NMR (CDCl$_3$, δppm): 3.8 (6H), 4.9–5.3 (4H), 5.9–6.1 (1H), 6.2 (1H, dd), 6.7 (1H, dd), 6.75–6.95 (5H), 7.2–7.6 (4H).

Elementary analysis for $C_{24}H_{22}N_2O_2S$: Calcd. (%): C, 71.62; H, 5.51; N, 6.96; Found (%): C, 71.89; H, 5.48; N, 6.91.

EXAMPLE 6

4,5-Bis(4-methoxyphenyl)-2-(1-propargylpyrrol-2-yl)thiazole (compound of the formula (I) wherein $R^1$=propargyl):

4,5-Bis(4-methoxyphenyl)-2-(pyrrol-2-yl)thiazole obtained in the same manner as described in Reference Example 6 (1.81 g, 5 mmole), propargyl bromide (1.18 g, 10 mmole), and tetra-n-butylammonium bromide (0.16 g, 0.5 mmole) are refluxed with vigorous stirring in two phases of dichloromethane (20 ml) and 50% aqueous sodium hydroxide (20 ml) for 5 minutes. To the mixture are added water and dichloromethane under ice-cooling, and the mixture is shaken. The dichloromethane layer is taken, and the aqueous layer is further extracted with dichloromethane. The dichloromethane layers are combined, dried over anhydrous magnesium sulfate, and distilled under reduced pressure to remove the solvent. The residue is recrystallized from n-hexane to give 4,5-bis(4-methoxyphenyl)-2-(1-propargylpyrrol-2-yl)thiazole (1.50 g, yield: 75%).

M.p. 101.5°–104.5° C.

NMR (CDCl$_3$, δppm): 2.45 (1H, t), 3.85 (6H), 5.45 (2H, d), 6.25 (1H, dd), 6.7 (1H, dd), 6.75–6.95 (5H), 7.2–7.6 (4H).

Elementary analysis for C$_{24}$H$_{20}$N$_2$O$_2$S: Calcd. (%): C, 71.97; H, 5.03; N, 7.00; Found (%): C, 72.17; H, 5.04; N, 7.09.

EXAMPLE 7

4,5-Bis(4-methoxyphenyl)-2-[1-(2,2,2-trifluoroethyl)-pyrrol-2-yl]thiazole (compound of the formula (I) wherein R$^1$=2,2,2-trifluoroethyl):

4,5-Bis(4-methoxyphenyl)-2-(pyrrol-2-yl)thiazole obtained in the same manner as described in Reference Example 6 (1.81 g, 5 mmole), 2,2,2-trifluoroethyl p-toluenesulfonate (1.27 g, 5 mmole), and tetra-n-butylammonium bromide (0.16 g, 0.5 mmole) are refluxed in two phases of benzene (20 ml) and 50% aqueous sodium hydroxide (20 ml) for 16 hours. To the mixture are added water and benzene under ice-cooling, and the mixture is shaken. The benzene layer is taken, and the aqueous layer is further extracted with benzene. The benzene layers are combined, dried over anhydrous magnesium sulfate, and distilled under reduced pressure to give an oily residue. The oily residue is subjected to silica gel column chromatography (solvent: benzene) and then is recrystallized from n-hexane to give 4,5-bis(4-methoxyphenyl)-2-[1-(2,2,2-trifluoroethyl)pyrrol-2-yl]thiazole (0.80 g, yield: 36%).

M.p. 108.5°–111.5° C.

NMR (CDCl$_3$, δppm): 3.8 (6H), 5.45 (2H, q), 6.25 (1H, dd), 6.65–6.95 (6H), 7.2–7.55 (4H).

Elementary analysis for C$_{23}$H$_{19}$N$_2$O$_2$SF$_3$: Calcd. (%): C, 62.15; H, 4.31; N, 6.30; Found (%): C, 62.13; H, 4.31; N, 6.45.

EXAMPLE 8

4,5-Bis(4-methoxyphenyl)-2-(1-isobutylpyrrol-2-yl)thiazole (compound of the formula (I) wherein R$^1$=isobutyl):

4,5-bis(4-methoxyphenyl)-2-(pyrrol-2-yl)thiazole obtained in the same manner as described in Reference Example 6 (1.81 g, 5 mmole) and metallic potassium (0.22 g, 5.5 mmole) are stirred in dimethoxyethane (40 ml) at room temperature for one hour, and thereto is added isobutyl bromide (2.74 g, 20 mmole). The mixture is refluxed for 2 hours. After distilling off the solvent, dichloromethane and water are added to the resulting residue, and the mixture is shaken. The dichloromethane layer is taken, dried over anhydrous magnesium sulfate and distilled under reduced pressure to remove the solvent. The residue is subjected to silica gel column chromatography (solvent, dichloromethane:cyclohexane=1:1), and then recrystallized from methanol to give 4,5-bis(4-methoxyphenyl)-2-(1-isobutylpyrrol-2-yl)thiazole (0.33 g, yield: 16%).

This product shows the same physiological properties as those of the product in Example 4.

EXAMPLES 9 TO 12

In the same manner as described in Example 8, the following compounds are prepared.

4,5-Bis(4-methoxyphenyl)-2-(1-ethylpyrrol-2-yl)thiazole (yield: 45%)

4,5-Bis(4-methoxyphenyl)-2-(1-isopropylpyrrol-2-yl)thiazole (yield: 32%)

4,5-Bis(4-methoxyphenyl)-2-(1-n-propylpyrrol-2-yl)thiazole (yield: 33%)

4,5-Bis(4-methoxyphenyl)-2-(1-allylpyrrol-2-yl)thiazole (yield: 50%)

These compounds show the same properties as those of the products in Examples described hereinbefore.

EXAMPLE 13

Methyl-2-[4,5-bis(4-methoxyphenyl)thiazol-2-yl]-pyrrole-1-acetate (compound of the formula (I) wherein R$^1$=—CH$_2$COOCH$_3$):

4,5-Bis(4-methoxyphenyl)-2-(pyrrol-2-yl)thiazole obtained in the same manner as described in Reference Example 6 (1.81 g, 5 mmole), methyl bromoacetate (0.84 g, 5.5 mmole), and tetra-n-butylammonium bromide (0.16 g, 0.5 mmole) are vigorously stirred in two phases of dichloromethane (20 ml) and 50% aqueous sodium hydroxide (20 ml) at room temperature for 2 minutes. To the mixture are added water and dichloromethane under ice-cooling, and the mixture is shaken. The dichloromethane layer is taken, and the aqueous layer is further extracted with dichloromethane. The dichloromethane layers are combined, dried over anhydrous magnesium sulfate, and distilled under reduced pressure to remove the solvent. The residue is subjected to silica gel column chromatography (solvent, dichloromethane:cyclohexane=1:1) and then is recrystallized from n-hexane to give methyl 2-[4,5-bis(4-methoxyphenyl)thiazol-2-yl]pyrrole-1-acetate (1.31 g, yield: 60%).

M.p. 171.5°–174.5° C.

NMR (CDCl$_3$, δppm): 3.7 (3H, s), 3.8 (6H), 5.25 (2H, s), 6.25 (1H, dd), 6.7–6.95 (6H), 7.2–7.5 (4H).

Elementary analysis for C$_{24}$H$_{22}$N$_2$O$_4$S:
Calcd. (%): C, 66.34; H, 5.10; N, 6.45; Found (%): C, 66.41; H, 4.99; N, 6.43.

EXAMPLE 14

Ethyl 2-[4,5-bis(4-methoxyphenyl)thiazol-2-yl]-pyrrole-1-acetate (compound of the formula (I) wherein R$^1$=—CH$_2$COOC$_2$H$_5$):

4,5-Bis(4-methoxyphenyl)-2-(pyrrol-2-yl)thiazole obtained in the same manner as described in Reference Example 6 (3.62 g, 10 mmole), ethyl bromoacetate (1.67 g, 10 mmole), and tetra-n-butylammonium bromide (0.32 g, 1 mmole) are refluxed with vigorous stirring in two phases of dichloromethane (40 ml) and 50% aqueous sodium hydroxide (40 ml) at room temperature for 2 minutes. To the mixture are added water and dichloromethane under ice-cooling, and the mixture is shaken. The dichloromethane layer is taken, and the aqueous layer is further extracted with dichloromethane. The dichloromethane layers are combined, dried over anhydrous magnesium sulfate, and distilled under reduced pressure to remove the solvent. The residue is recrystallized from ligroin to give ethyl 2-[4,5-bis(4-methoxyphenyl)thiazol-2-yl]pyrrole-1-acetate (3.64 g, yield: 81%).

M.p. 132.5°–135.5° C.

NMR (CDCl$_3$, δppm): 1.2 (3H, t), 3.8 (6H), 4.15 (2H, q), 5.25 (2H, s), 6.25 (1H, dd), 6.7–6.95 (6H), 7.2–7.55 (4H).

Elementary analysis for C$_{25}$H$_{24}$N$_2$O$_4$S: Calcd. (%): C, 66.95; H, 5.39; N, 6.25; Found (%): C, 67.17; H, 5.40; N, 6.19.

EXAMPLE 15 n-Propyl 2-[4,5-bis(4-methoxyphenyl)thiazol-2-yl]-pyrrole-1-acetate (compound of the formula (I) wherein R$^1$=—CH$_2$COO—n—C$_3$H$_7$):

2-[4,5-Bis(4-methoxyphenyl)thiazol-2-]pyrrole-1-acetic acid obtained in the same manner as described in Reference Example 7 (2.10 g, 5 mmole) and conc-sulfuric acid (100 mg) are refluxed in n-propanol (100 ml) for 20 minutes. After distilling off the slvent under reduced pressure, the residue is subjected to silica gel column chromatography (solvent, dichloromethane), and is recrystallized from cyclohexane to give n-propyl 2-[4,5-bis(4-methoxyphenyl)-thiazol-2-yl]pyrrole-1-acetate (1.40 g, yield: 61%).

M.p. 94.0°–97.0° C.

NMR (CDCl$_3$, δppm): 0.8 (3H, t), 1.4–1.75 (2H), 3.8 (6H), 4.05 (2H, t), 5.25 (2H, s), 6.25 (1H, dd), 6.65–6.9 (6H), 7.2–7.5 (4H).

Elementary analysis for C$_{26}$H$_{26}$N$_2$O$_4$S: Calcd. (%): C, 67.51; H, 5.67; N, 6.06; Found (%): C, 67.75; H, 5.48; N, 6.20.

EXAMPLE 16

Isopropyl 2-[4,5-bis(4-methoxyphyenyl)thiazol-2-yl]pyrrole-1-acetate (compound of the formula (I) wherein R$^1$=—CH$_2$COO—iso—C$_3$H$_7$):

In the same manner as described in Example 15 except that isopropanol is used instead of n-propanol and the reflux time is two hours, there is obtained isopropyl 2-[4,5-bis(4-methoxyphenyl)thiazol-2-yl]pyrrole-1-acetate (1.40 g, yield: 61%).

M.p. 130.0°–133.0° C.

NMR (CDCl$_3$, δppm): 1.15 (6H, d), 3.8 (6H), 4.8–5.15 (1H), 5.25 (2H, s), 6.25 (1H, dd), 6.65–6.9 (6H), 7.2–7.5 (4H).

Elementary analysis for C$_{26}$H$_{26}$N$_2$O$_4$S: Calcd. (%): C, 67.51; H, 5.67; N, 6.06; Found (%): C, 67.78; H, 5.64; N, 6.10.

EXAMPLE 17 n-Butyl 2-[4,5-bis(4-methoxyphenyl)thiazol-2-yl]-pyrrole-1-acetate (compound of the formula (I) wherein R$^1$=—CH$_2$COO—n—C$_4$H$_9$):

2-[4,5-Bis(4-methoxyphenyl)thiazol-2-]pyrrole-1-acetic acid obtained in the same manner as described in Reference Example 7 (1.68 g, 4 mmole), n-butanol (0.30 g, 4 mmole) and p-toluenesulfonic acid (95 mg, 0.5 mmole) are refluxed in benzene (50 ml) for 8 hours while distilling off water by azeotrope. After allowing to cool, benzene is distilled off under reduced pressure. The residue is subjected to silica gel column chromatography (solvent, dichloromethane), and is recrystallized from cyclohexane to give n-butyl 2-[4,5-bis(4-methoxyphenyl)thiazol-2-yl]-pyrrole-1-acetate (1.20 g, yield: 63%).

M.p. 98.0°–101.0° C.

NMR (CDCl$_3$, δppm): 0.85 (3H, t), 1.1–1.7 (4H), 3.85 (6H), 4.1 (2H, t), 5.3 (2H, s), 6.25 (1H, dd), 6.7–6.95 (6H), 7.2–7.5 (4H).

Elementary analysis for C$_{27}$H$_{28}$N$_2$O$_4$S: Calcd. (%): C, 68.04; H, 5.92; N, 5.88; Found (%): C, 68.19; H, 6.03; N, 5.99.

EXAMPLE 18

Isobutyl 2-[4,5-bis(4-methoxyphenyl)thiazol-2-yl]-pyrrole-1-acetate (compound of the formula (I) wherein R$^1$=—CH$_2$COO—iso—C$_4$H$_9$):

4,5-Bis(4-methoxyphenyl)-2-(pyrrol-2-yl)thiazole obtained in the same manner as described in Reference Example 6 (1.81 g, 5 mmole), isobutyl bromoacetate (1.07 g, 5.5 mmole), and tetra-n-butylammonium bromide (0.16 g, 0.5 mmole) are vigorously stirred in two phases of dichloromethane (20 ml) and 50% aqueous sodium hydroxide (20 ml) at room temperature for 2 minutes. To the mixture are added water and dichloromethane under ice-cooling, and the mixture is shaken. The dichloromethane layer is taken, and the aqueous layer is further extracted with dichloromethane. The dichloromethane layers are combined, washed with water, dried over anhydrous magnesium sulfate, and distilled under reduced pressure to remove the solvent. The residue is subjected to silica gel column chromatography (solvent, dichloromethane:cyclohexane=1:1) and is recrystallized from n-hexane to give isobutyl 2-[4,5-bis(4-methoxyphenyl)-thiazol-2-yl]pyrrole-1-acetate (1.31 g, yield: 55%).

M.p. 105.5°–108.5° C.

NMR (CDCl$_3$, δppm): 0.8 (6H, d), 1.7–2.0 (1H), 3.5–3.95 (8H), 5.3 (2H, s), 6.25 (1H, dd), 6.7–6.95 (6H), 7.2–7.5 (4H).

Elementary analysis for C$_{27}$H$_{28}$N$_2$O$_4$S: Calcd. (%): C, 68.04; H, 5.92; N, 5.88; Found (%): C, 67.92; H, 5.87; N, 5.92.

EXAMPLE 19 sec-Butyl 2-[4,5-bis(4-methoxyphenyl)thiazol-2-yl]pyrrole-1-acetate (compound of the formula (I) wherein R$^1$=—CH$_2$COO—sec—C$_4$H$_9$):

In the same manner as described in Example 18 except that sec-butyl bromoacetate (1.07 g, 5.5 mmole) is used instead of isobutyl bromoacetate, there is obtained sec-butyl 2-[4,5-bis(4-methoxyphenyl)thiazol-2-yl]pyrrole-1-acetate (1.67 g, yield: 70%).

M.p. 102.5°–105.5° C.

NMR (CDCl$_3$, δppm): 0.75 (3H, t), 1.05 (3H, d), 1.3–1.65 (2H), 3.8 (6H), 4.85 (1H, q), 5.3 (2H, s), 6.2 (1H, dd), 6.65–6.9 (6H), 7.2–7.5 (4H).

Elementary analysis for C$_{27}$H$_{28}$N$_2$O$_4$S: Calcd. (%): C, 68.04; H, 5.92; N, 5.88; Found (%): C, 68.13; H, 5.95; N, 5.99.

EXAMPLE 20 n-Pentyl 2-[4,5-bis(4-methoxyphenyl)thiazol-2-yl]-pyrrole-1-acetate (compound of the formula (I) wherein R$^1$=—CH$_2$COO—n—C$_5$H$_{11}$):

2-[4,5-Bis(4-methoxyphenyl)thiazol-2-]pyrrole-1-acetic acid obtained in the same manner as described in Reference Example 7 (2.10 g, 5 mmole), n-pentanol (1.76 g, 20 mmole) and conc-sulfuric acid (200 mg) are refluxed in benzene (50 ml) for 2 hours while distilling off water by azeotrope. After allowering to cool, benzene is distilled off under reduced pressure. The residue is subjected to silica gel column chromatography (solvent, dichloromethane), and is recrystallized from n-hexane to give n-pentyl 2-[4,5-bis(4-methoxyphenyl)-thiazol-2-yl]pyrrole-1-acetate (1.14 g, yield: 46%).

M.p. 101.0°–104.0° C.

NMR (CDCl$_3$, δppm): 0.85 (3H, t), 1.1–1.7 (6H), 3.8 (6H), 4.1 (2H, s), 5.3 (2H, s), 6.25 (1H, dd), 6.7–6.95 (6H), 7.2–7.5 (4H).

Elementary analysis for C$_{28}$H$_{30}$N$_2$O$_4$S: Calcd. (%): C, 68.55; H, 6.16; N, 5.71; Found (%): C, 68.61; H, 6.02; N, 5.76.

EXAMPLE 21

Isopentyl 2-[4,5-bis(4-methoxyphenyl)thiazol-2-yl]pyrrole-1-acetate (compound of the formula (I) wherein R$^1$=—CH$_2$COO—iso—C$_5$H$_{11}$):

In the same manner as described in Example 20 except that isopentanol (1.76 g, 20 mmole) is used instead of n-pentanol, there is obtained isopentyl 2-[4,5-bis(4-methoxyphenyl)thiazol-2-yl]pyrrole-1-acetate (1.13 g, yield: 46%).

M.p. 98.5°–101.5° C.

NMR (CDCl$_3$, δppm): 0.8 (6H, d), 1.3–1.7 (3H), 3.8 (6H), 4.1 (2H, t), 5.3 (2H, s), 6.25 (1H, dd), 6.7–6.95 (6H), 7.2–7.5 (4H).

Elementary analysis for C$_{28}$H$_{30}$N$_2$O$_4$S: Calcd. (%): C, 68.55; H, 6.16; N, 5.71; Found (%): C, 68.29; H, 6.17; N, 5.81.

EXAMPLE 22

Neopentyl 2-[4,5-bis(4-methoxyphenyl)thiazol-2-yl]pyrrole-1-acetate (compound of the formula (I) wherein R$^1$=—CH$_2$COO—neo—C$_5$H$_{11}$):

In the same manner as described in Example 18 except that neopentyl bromoacetate (1.15 g, 5.5 mmole) is used instead of isobutyl bromoacetate, there is obtained neopentyl 2-[4,5-bis(4-methoxyphenyl)thiazol-2-yl]pyrrole-1-acetate (1.72 g, yield: 70%).

M.p. 114.5°–117.5° C.

NMR (CDCl$_3$, δppm): 0.8 (9H, s), 3.8 (6H), 5.35 (2H, s), 6.25 (1H, dd), 6.7–6.95 (6H), 7.2–7.5 (4H).

Elementary analysis for C$_{28}$H$_{30}$N$_2$O$_4$S: Calcd. (%): C, 68.55; H, 6.16; N, 5.71; Found (%): C, 68.45; H, 6.32; N, 5.64.

EXAMPLE 23

2-Methyl-1-butyl 2-[4,5-bis(4-methoxyphenyl)-thiazol-2-yl]pyrrole-1-acetate (compound of the formula (I) wherein

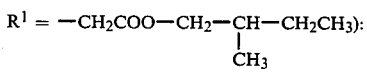

In the same manner as described in Example 20 except that 2-methyl-1-butanol (1.76 g, 20 mmole) is used instead of n-pentanol, there is obtained 2-methyl-1-butyl 2-[4,5-bis(4-methoxyphenyl)thiazol-2-yl]pyrrole-1-acetate (0.83 g, yield: 34%).

M.p. 81.5°–84.5° C.

NMR (CDCl$_3$, δppm): 0.7–0.9 (6H), 1.0–1.8 (3H), 3.8 (6H), 3.85–4.05 (2H), 5.3 (2H, s), 6.25 (1H, dd), 6.7–6.95 (6H), 7.2–7.5 (4H).

Elementary analysis for C$_{28}$H$_{30}$N$_2$O$_4$S: Calcd. (%): C, 68.55; H, 6.16; N, 5.71; Found (%): C, 68.20; H, 6.10; N, 5.83.

EXAMPLE 24

2-Pentyl 2-[4,5-bis(4-methoxyphenyl)thiazol-2-yl]-pyrrole-1-acetate (compound of the formula (I) wherein

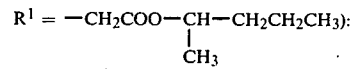

In the same manner as described in Example 20 except that 2-pentanol (1.76 g, 20 mmole) is used instead of n-pentanol, there is obtained 2-pentyl 2-[4,5-bis(4-methoxyphenyl)thiazol-2-yl]pyrrole-1-acetate (1.64 g, yield: 67%).

M.p. 81.0°–84.0° C.

NMR (CDCl$_3$, δppm): 0.65–0.9 (3H), 1.0–1.65 (7H), 3.85 (6H), 4.75–5.1 (1H), 5.3 (2H, s), 6.25 (1H, dd), 6.7–6.95 (6H), 7.2–7.55 (4H).

Elementary analysis for C$_{28}$H$_{30}$N$_2$O$_4$S: Calcd. (%): C, 68.55; H, 6.16; N, 5.71; Found (%): C, 68.81; H, 6.33; N, 5.85.

EXAMPLE 25

3-Pentyl 2-[4,5-bis(4-methoxyphenyl)thiazol-2-yl]-pyrrole-1-acetate (compound of the formula (I) wherein

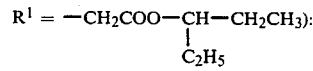

In the same manner as described in Example 20 except that 3-pentanol (1.76 g, 20 mmole) is used instead of n-pentanol, there is obtained 3-pentyl 2-[4,5-bis(4-methoxyphenyl)thiazol-2-yl]pyrrole-1-acetate (1.69 g, yield: 69%).

M.p. 94.0°–97.0° C.

NMR (CDCl$_3$, δppm): 0.75 (6H, t), 1.3–1.65 (4H), 3.85 (6H), 4.9 (1H, quintet), 5.4 (2H, s), 6.25 (1H, dd), 6.7–6.95 (6H), 7.2–7.55 (4H).

Elementary analysis for C$_{28}$H$_{30}$N$_2$O$_4$S: Calcd. (%): C, 68.55; H, 6.16; N, 5.71; Found (%): C, 68.80; H, 6.25; N, 5.76.

EXAMPLE 26

3-Methyl-2-butyl 2-[4,5-bis(4-methoxyphenyl)-thiazol-2-yl]pyrrole-1-acetate (compound of the formula (I) wherein

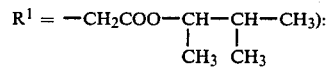

In the same manner as described in Example 20 except that 3-methyl-2-butanol (1.76 g, 20 mmole) is used instead of n-pentanol, there is obtained 3-methyl-2-butyl 2-[4,5-bis(4-methoxyphenyl)thiazol-2-yl]pyrrole-1-acetate (0.71 g, yield: 29%).

M.p. 88.5°–91.5° C.

NMR (CDCl$_3$, δppm): 0.75 (6H, d), 1.0 (3H, d), 1.5–1.9 (1H), 3.85 (6H), 4.65–4.9 (1H), 5.35 (2H, s), 6.25 (1H, dd), 6.7–6.95 (6H), 7.2–7.55 (4H).

Elementary analysis for C$_{28}$H$_{30}$N$_2$O$_4$S: Calcd. (%): C, 68.55; H, 6.16; N, 5.71; Found (%): C, 68.37; H, 6.26; N, 5.72.

EXAMPLE 27 n-Hexyl 2-[4,5-bis(4-methoxyphenyl)thiazol-2-yl]-pyrrole-1-acetate (compound of the formula (I) wherein R$^1$=—CH$_2$COO—n—C$_6$H$_{13}$):

In the same manner as described in Example 18 except that n-hexyl bromoacetate (1.23 g, 5.5 mmole) is used instead of isobutyl bromoacetate, there is obtained n-hexyl 2-[4,5-bis(4-methoxyphenyl)thiazol-2-yl]pyrrole-1-acetate (2.12 g, yield: 76%).

M.p. 102.0°–105.0° C.

NMR (CDCl$_3$, δppm): 0.85 (3H), 1.1–1.65 (8H), 3.8 (6H), 4.1 (2H, t), 5.25 (2H, s), 6.25 (1H, dd), 6.7–6.95 (6H), 7.2–7.5 (4H).

Elementary analysis for C$_{29}$H$_{32}$N$_2$O$_4$S: Calcd. (%): C, 69.02; H, 6.39; N, 5.55; Found (%): C, 69.20; H, 6.28; N, 5.71.

EXAMPLE 28 n-Octyl 2-[4,5-bis(4-methoxyphenyl)thiazol-2-yl]-pyrrole-1-acetate (compound of the formula (I) wherein R$^1$=—CH$_2$COO—n—octyl):

In the same manner as described in Example 20 except that n-octanol (2.60 g, 20 mmole) is used instead of n-pentanol, there is obtained n-octyl 2-[4,5-bis(4-methoxyphenyl)thiazol-2-yl]pyrrole-1-acetate (1.15 g, yield: 43%).

M.p. 84.5°–87.5° C.

NMR (CDCl$_3$, δppm): 0.9 (3H), 1.1–1.7 (12H), 3.85 (3H, s), 3.9 (3H, s), 4.1 (2H, t), 5.3 (2H), 6.25 (1H, dd), 6.7–6.95 (6H), 7.2–7.55 (4H).

Elementary analysis for C$_{31}$H$_{36}$N$_2$O$_4$S: Calcd. (%): C, 69.90; H, 6.81; N, 5.26; Found (%): C, 70.01; H, 7.02; N, 5.30.

EXAMPLE 29

Allyl 2-[4,5-bis(4-methoxyphenyl)thiazol-2-yl]-pyrrole-1-acetate (compound of the formula (I) wherein R$^1$=—CH$_2$COO—allyl):

In the same manner as described in Example 18 except that allyl bromoacetate (0.98 g, 5.5 mmole) is used instead of isobutyl bromoacetate, there is obtained allyl 2-[4,5-bis(4-methoxyphenyl)thiazol-2-yl]pyrrole-1-acetate (1.66 g, yield: 72%).

M.p. 97.0°–100.0° C.

NMR (CDCl$_3$, δppm): 3.85 (6H), 4.55–4.65 (2H), 5.1–5.35 (4H), 5.6–6.0 (1H), 6.25 (1H, dd), 6.7–6.95 (6H), 7.2–7.55 (4H).

Elementary analysis for C$_{26}$H$_{24}$N$_2$O$_4$S: Calcd. (%): C, 67.81; H, 5.25; N, 6.08; Found (%): C, 67.89; H, 5.32; N, 6.32.

EXAMPLE 30

Propargyl 2-[4,5-bis(4-methoxyphenyl)thiazol-2-yl]pyrrole-1-acetate (compound of the formula (I) wherein R$^1$=—CH$_2$COO—propargyl):

4,5-Bis(4-methoxyphenyl)-2-(pyrrol-2-yl)thiazole obtained in the same manner as described in Reference Example 6 (2.19 g, 6 mmole) and potassium tert-butoxide (0.71 g, 6.3 mmole) are stirred in DMF (10 ml) at room temperature for one hour, and thereto is added propargyl bromoacetate (1.17 g, 6.6 mmole), and the mixture is stirred for 24 hours. To the mixture are added water and ethyl acetate. The ethyl acetate layer is taken, washed with water, dried over anhydrous magnesium sulfate, and distilled under reduced pressure to remove the solvent. The residue is subjected to silica gel column chromatography (solvent, cyclohexane:dichloromethane=1:1) and is recrystallized from cyclohexane to give propargyl 2-[4,5-bis(4-methoxyphenyl)thiazol-2-yl]pyrrole-1-acetate (1.62 g, yield: 59%).

M.p. 100.0°–103.0° C.

NMR (CDCl$_3$, δppm): 2.45 (1H, t), 3.8 (6H), 4.65 (2H, d), 5.3 (2H, s), 6.25 (1H, dd), 6.65–6.9 (6H), 7.2–7.5 (4H).

Elementary analysis for C$_{26}$H$_{22}$N$_2$O$_4$S: Calcd. (%): C, 68.10; H, 4.84; N, 6.11; Found (%): C, 68.29; H, 4.70; N, 6.05.

EXAMPLE 31

Benzyl 2-[4,5-bis(4-methoxyphenyl)thiazol-2-yl]-pyrrole-1-acetate (compound of the formula (I) wherein R$^1$=—CH$_2$COO—benzyl):

In the same manner as described in Example 18 except that benzyl bromoacetate (1.26 g, 5.5 mmole) is used instead of isobutyl bromoacetate, there is obtained benzyl 2-[4,5-bis(4-methoxyphenyl)thiazol-2-yl]pyrrole-1-acetate (0.92 g, yield: 36%).

M.p. 152.0°–154.5° C.

NMR (CDCl$_3$, δppm): 3.80 (3H, s), 3.85 (3H, s), 5.1 (2H, s), 5.3 (2H, s), 6.25 (1H, dd), 6.7–6.9 (6H), 7.15–7.5 (9H).

Elementary analysis for C$_{30}$H$_{26}$N$_2$O$_4$S: Calcd. (%): C, 70.57; H, 5.13; N, 5.49; Found (%): C, 70.49; H, 5.02; N, 5.41.

EXAMPLES 32 TO 35

In the same manner as described in Example 20, the following compounds are prepared.

Isobutyl 2-[4,5-bis(4-methoxyphenyl)thiazol-2-yl]-pyrrole-1-acetate (yield: 34%)

sec-Butyl 2-[4,5-bis(4-methoxyphenyl)thiazol-2-yl]pyrrole-1-acetate (yield: 41%)

Neopentyl 2-[4,5-bis(4-methoxyphenyl)thiazol-2-yl]pyrrole-1-acetate (yield: 22%)

n-Hexyl 2-[4,5-bis(4-methoxyphenyl)thiazol-2-yl]-pyrrole-1-acetate (yield: 46%)

These compounds show the same properties as those of the products in Examples as described hereinbefore.

EXAMPLE 36

4,5-Bis(4-methoxyphenyl)-2-(1-ethoxymethylpyrrol-2-yl)thiazole (compound of the formula (I) wherein R$^1$=—CH$_2$OC$_2$H$_5$):

4,5-Bis(4-methoxyphenyl)-2-(pyrrol-2-yl)thiazole obtained in the same manner as described in Reference Example 6 (1.81 g, 5 mmole), chloromethyl ethyl ether (0.57 g, 6 mmole), and tetra-n-butylammonium bromide (0.16 g, 0.5 mmole) are refluxed in two phases of benzene (20 ml) and 50% aqueous sodium hydroxide (20 ml) for 20 minutes. To the mixture are added water and benzene under ice-cooling, and the mixture is shaken. The benzene layer is taken, washed with water, dried over anhydrous magnesium sulfate, and distilled under reduced pressure to remove the solvent. The residue is subjected to silica gel column chromatography (solvent, ethyl acetate:cyclohexane=1:20) and is recrystallized from n-hexane to give 4,5-bis(4-methoxyphenyl)-2-(1-ethoxymethylpyrrol-2-yl)thiazole (1.01 g, yield: 48%).

M.p. 49.0°–52.0° C.

NMR (CDCl$_3$, δppm): 1.15 (3H, t), 3.5 (2H, q), 3.8 (6H), 5.85 (2H, s), 6.2 (1H, dd), 6.6–7.0 (6H), 7.2–7.55 (4H).

Elementary analysis for C$_{24}$H$_{24}$N$_2$O$_3$S: Calcd. (%): C, 68.55; H, 5.75; N, 6.66; Found (%): C, 68.50; H, 5.84; N, 6.68.

EXAMPLE 37

4,5-Bis(4-methoxyphenyl)-2-(1-n-propoxymethylpyrrol-2-yl)thiazole (compound of the formula (I) wherein R$^1$=—CH$_2$—n—C$_3$H$_7$):

4,5-Bis(4-methoxyphenyl)-2-(pyrrol-2-yl)thiazole obtained in the same manner as described in Reference Example 6 (1.81 g, 5 mmole), chloromethyl n-propyl ether (0.65 g, 6 mmole), and tetra-n-butylammonium bromide (0.16 g, 0.5 mmole) are refluxed in two phases of benzene (20 ml) and 50% aqueous sodium hydroxide (20 ml) for 20 minutes. To the mixture are added water and benzene under ice-cooling, and the mixture is shaken. The benzene layer is taken, washed with water, dried over anhydrous magnesium sulfate, and distilled under reduced pressure to remove the solvent. The residue is subjected to silica gel column chromatography (solvent, ethyl acetate:cyclohexane=1:20) to give oily 4,5-bis(4-methoxyphenyl)-2-(1-n-propoxymethylpyrrol-2-yl)thiazole (1.80 g, yield: 83%).

NMR (CDCl$_3$, δppm): 0.85 (3H, t), 1.35-1.75 (2H), 3.45 (2H, t), 3.8 (6H), 5.9 (2H, s), 6.2 (1H, dd), 6.6-7.0 (6H), 7.2-7.55 (4H).

Elementary analysis for $C_{25}H_{26}N_2O_3S$: Calcd. (%): C, 69.10; H, 6.03; N, 6.45; Found (%): C, 69.41; H, 6.22; N, 6.19.

EXAMPLE 38

4,5-Bis(4-methoxyphenyl)-2-[1-(2-ethoxyethyl)-pyrrol-2-yl]thiazole (compound of the formula (I) wherein $R^1 = -CH_2CH_2O-C_2H_5$):

4,5-Bis(4-methoxyphenyl)-2-(pyrrol-2-yl)thiazole obtained in the same manner as described in Reference Example 6 (1.81 g, 5 mmole), 2-bromoethyl ethyl ether (0.92 g, 6 mmole), and tetra-n-butylammonium bromide (0.16 g, 0.5 mmole) are refluxed in two phases of benzene (20 ml) and 50% aqueous sodium hydroxide (20 ml) for 4 hours. To the mixture are added water and benzene under ice-cooling, and the mixture is shaken. The benzene layer is taken, washed with water, dried over anhydrous magnesium sulfate, and distilled under reduced pressure to remove the solvent. The residue is subjected to silica gel column chromatography (solvent, ethyl acetate:cyclohexane=1:20) and is recrystallized from n-hexane to give 4,5-bis(4-methoxyphenyl)-2-[1-(2-ethoxyethyl)pyrrol-2-yl]thiazole (0.96 g, yield: 44%).

M.p. 68.0°-71.0° C.

NMR (CDCl$_3$, δppm): 1.15 (3H, t), 3.5 (2H, q), 3.8-3.9 (8H), 4.7 (2H, t), 6.15 (1H, dd), 6.6-6.9 (6H), 7.2-7.55 (4H).

Elementary analysis for $C_{25}H_{26}N_2O_3S$: Calcd. (%): C, 69.10; H, 6.03; N, 6.45; Found (%): C, 69.21; H, 6.00; N, 6.49.

EXAMPLE 39

4,5-Bis(4-methoxyphenyl)-2-[1-(2-vinyloxyethyl)-pyrrol-2-yl]thiazole (compound of the formula (I) wherein $R^1 = -CH_2CH_2O-CH=CH_2$):

4,5-Bis(4-methoxyphenyl)-2-(pyrrol-2-yl)thiazole obtained in the same manner as described in Reference Example 6 (2.19 g, 6 mmole) and potassium tert-butoxide (0.71 g, 6.3 mmole) are stirred in DMF (10 ml) at room temperature for one hour, and thereto is added 2-chloroethyl vinyl ether (0.70 g, 6.3 mmole), and the mixture is stirred at room temperature for 30 minutes. To the mixture are added water and ethyl acetate, and the mixture is shaken. The ethyl acetate layer is taken, washed with water, dried over anhydrous magnesium sulfate, and distilled under reduced pressure to remove the solvent. The residue is subjected to silica gel column chromatography (solvent, cyclohexane:ethyl acetate=20:1) and is recrystallized from n-hexane to give 4,5-bis(4-methoxyphenyl)-2-[1-(2-vinyloxyethyl)pyrrol-2-yl]thiazole (1.36 g, yield: 63%).

M.p. 81.5°-84.5° C.

NMR (CDCl$_3$, δppm): 3.8 (6H), 3.95-4.3 (4H), 4.75 (2H, t), 6.15 (1H, dd), 6.4 (1H, dd), 6.65-6.9 (6H), 7.2-7.55 (4H).

Elementary analysis for $C_{25}H_{24}N_2O_3S$: Calcd. (%): C, 69.42; H, 5.59; N, 6.48; Found (%): C, 69.40; H, 5.42; N, 6.60.

EXAMPLE 40

4,5-Bis(4-methoxyphenyl)-2-[1-(2-ethylthioethyl)-pyrrol-2-yl]thiazole (compound of the formula (I) wherein $R^1 = -CH_2CH_2S-C_2H_5$):

4,5-Bis(4-methoxyphenyl)-2-(pyrrol-2-yl)thiazole obtained in the same manner as described in Reference Example 6 (1.81 g, 5 mmole), 2-bromoethyl ethyl sulfide (1.01 g, 6 mmole), and tetra-n-butylammonium bromide (0.16 g, 0.5 mmole) are refluxed in two phases of benzene (20 ml) and 50% aqueous sodium hydroxide (20 ml) for 4 hours. To the mixture are added water and benzene under ice-cooling, and the mixture is shaken. The benzene layer is taken, washed with water, dried over anhydrous magnesium sulfate, and distilled under reduced pressure to remove the solvent. The residue is subjected to silica gel column chromatography (solvent, ethyl acetate:cyclohexane=1:20) to give oily 4,5-bis(4-methoxyphenyl)-2-[1-(2-ethylthioethyl)pyrrol-2-yl]thiazole (2.01 g, yield: 89%).

NMR (CDCl$_3$, δppm): 1.1 (3H, t), 2.45 (2H, q), 3.0 (2H, dd), 3.8 (6H), 4.65 (2H, dd), 6.15 (1H, dd), 6.6-6.9 (6H), 7.2-7.55 (4H).

Elementary analysis for $C_{25}H_{26}N_2O_2S_2$: Calcd. (%): C, 66.63; H, 5.82; N, 6.22; Found (%): C, 66.51; H, 5.78; N, 6.21.

EXAMPLE 41

4,5-Bis(4-methoxyphenyl)-2-[1-(3-ethoxypropyl)-pyrrol-2-yl]thiazole (compound of the formula (1) wherein $R^1 = -CH_2CH_2CH_2O-C_2H_5$):

In the same manner as described in Example 40 except that 3-bromopropyl ethyl ether (1.00 g, 6 mmole) is used instead of 2-bromoethyl ethyl sulfide, there is obtained oily 4,5-bis(4-methoxyphenyl)-2-[1-(3-ethoxypropyl)pyrrol-2-yl]thiazole (0.50 g, yield: 22%).

NMR (CDCl$_3$, δppm): 1.2 (3H, t), 2.0-2.35 (2H), 3.4-3.6 (4H), 3.85 (6H), 4.65 (2H, t), 6.2 (1H, dd), 6.65-6.95 (6H), 7.2-7.6 (4H).

Elementary analysis for $C_{26}H_{28}N_2O_3S$: Calcd. (%): C, 69.61; H, 6.29; N, 6.25; Found (%): C, 69.41; H, 6.28; N, 6.17.

EXAMPLE 42

Preparation of tablets:

Compressed tablets containing as an active ingredient allyl 2-[4,5-bis(4-methoxyphenyl)thiazol-2-yl]-pyrrole-1-acetate (compound in Example 29) (2 mg per one tablet) are prepared by the following formula.

| Components | Amount (g) |
|---|---|
| [Formula] | |
| Compound in Example 29 | 40 |
| Crystalline cellulose | 1580 |
| Lactose | 1600 |
| Carboxymethyl cellulose calcium | 120 |
| Talc | 40 |

| Components | Amount (g) |
| --- | --- |
| Magnesium stearate | 20 |

The above components are uniformly mixed and the mixture is tableted by a conventional method to give tablets.

EXAMPLE 43

Preparation of powders:

Powders containing as an active ingredient 4,5-bis(4-methoxyphenyl)-2-(1-allylpyrrol-2-yl)thiazole (compound in Example 5) (2 mg per 1 g of the powder) are prepared by the following formula.

| Components | Amount (g) |
| --- | --- |
| [Formula] | |
| Compound in Example 5 | 2 |
| Lactose | 598 |
| Starch | 400 |

The above components are uniformly mixed to give powders.

EXAMPLE 44

Preparation of powders:

Powders containing as an active ingredient 4,5-bis(4-methoxyphenyl)-2-[1-(2-ethylthioethyl)pyrrol-2-yl]-thiazole (compound in Example 40) (2 mg per 1 g of the powder) are prepared by the following formula.

| Components | Amount (g) |
| --- | --- |
| [Formula] | |
| Compound in Example 40 | 2 |
| Lactose | 300 |
| Crystalline cellulose | 400 |
| Starch | 298 |

The above components are uniformly mixed to give powders.

EXAMPLE 45

Preparation of hard capsules:

Hard capsules containing as an active ingredient 4,5-bis(4-methoxyphenyl)-2-[1-(2-ethoxyethyl)pyrrol-2-yl]-thiazole (compound in Example 38) (2 mg per one capsule) are prepared by the following formula.

| Components | Amount (g) |
| --- | --- |
| [Formula] | |
| Compound in Example 38 | 40 |
| Crystalline cellulose | 880 |
| Lactose | 2000 |
| Talc | 60 |
| Magnesium stearate | 20 |

The above components are uniformly mixed and the powders are packed in #3 hard capsules.

EXAMPLE 46

Preparation of soft capsules:

Soft capsules containing as an active ingredient propargyl 2-[4,5-bis(4-methoxyphenyl)thiazol-2-yl]pyrrole-1-acetate (compound in Example 30) (2 mg per one capsule) are prepared by the following formulae.

| Components | Amount (g) |
| --- | --- |
| [Formula 1] | |
| Compound in Example 30 | 40 |
| Corn oil | 1960 |
| [Formula 2] | |
| Gelatin | 2000 |
| Glycerine | 660 |
| Methyl p-hydroxybenzoate | 4 |
| Propyl p-hydroxybenzoate | 1 |
| Purified water | 1600 |

The compound in Example 30 is dissolved in corn oil as in Formula 1, and the liquid mixture is embraced with gelatin membrane prepared by Formula 2 to give soft capsules.

What is claimed is:

1. A 4,5-bis(4-methoxyphenyl)-2-(pyrrol-2-yl)-thiazole compound of the formula:

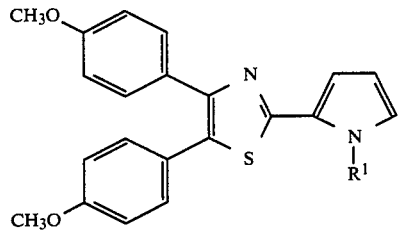

wherein $R^1$ is $C_{1-4}$ alkyl, $C_{2-4}$ alkenyl, $C_{2-4}$ alkynyl, 2,2,2-trifluoroethyl, a group of the formula: $-CH_2COOR^2$ ($R^2$ is $C_{1-8}$ alkyl, $C_{2-4}$ alkenyl, $C_{2-4}$ alkynyl, or phenyl-$C_{1-2}$ alkyl), or a group of the formula: $-(CH_2)_n-A-R^3$ (A is oxygen or sulfur, $R^3$ is $C_{1-4}$ alkyl or $C_{2-4}$ alkenyl, and n is 1, 2 or 3).

2. The compound according to claim 1, wherein $R^1$ is $C_{1-4}$ alkyl, $C_{2-4}$ alkenyl, $C_{2-4}$ alkynyl, 2,2,2-trifluoroethyl.

3. The compound according to claim 1, wherein $R^1$ a group of the formula: $-CH_2COOR^2$ ($R^2$ is $C_{1-8}$ alkyl, $C_{2-4}$ alkenyl, $C_{2-4}$ alkynyl, or phenyl-$C_{1-2}$ alkyl).

4. The compound according to claim 3, wherein $R^2$ is a member selected from ethyl, n-propyl, isopropyl, n-butyl, isobutyl, sec-butyl, isopentyl, neopentyl, 2-methyl-1-butyl, 2-pentyl, 3-pentyl, allyl, propargyl, and benzyl.

5. The compound according to claim 1, wherein $R^1$ a group of the formula: $-(CH_2)_n-A-R^3$ (A is oxygen or sulfur, $R^3$ is $C_{1-4}$ alkyl or $C_{2-4}$ alkenyl, and n is 1, 2 or 3).

6. The compound according to claim 5, wherein $R^3$ is ethyl.

7. A pharmaceutical composition useful for prophylaxis and treatment of platelet aggregation diseases, which comprises as an active ingredient an effective amount of a 4,5-bis(4-methoxyphenyl)-2-(pyrrol-2-yl)thiazole compound of the formula:

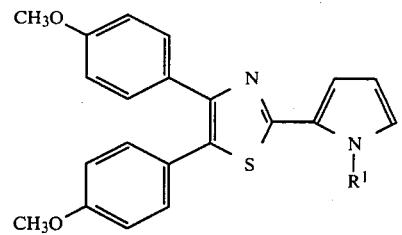
wherein $R^1$ is $C_{1-4}$ alkyl, $C_{2-4}$ alkenyl, $C_{2-4}$ alkynyl, 2,2,2-trifluoroethyl, a group of the formula: —$CH_2COOR^2$ ($R^2$ is $C_{1-8}$ alkyl, $C_{2-4}$ alkenyl, $C_{2-4}$ alkynyl, or phenyl-$C_{1-2}$ alkyl), or a group of the formula: —$(CH_2)_n$—A—$R^3$ (A is oxygen or sulfur, $R^3$ is $C_{1-4}$ alkyl or $C_{2-4}$ alkenyl, and n is 1, 2 or 3) in admixture with a conventional pharmaceutically acceptable carrier or diluent.
* * * * *